(12) United States Patent
Shapiro et al.

(10) Patent No.: US 7,329,269 B2
(45) Date of Patent: Feb. 12, 2008

(54) INTRAVASCULAR FILTERING DEVICES AND METHODS

(75) Inventors: Gary Shapiro, Medfield, MA (US); David Blossom, Wellesley, MA (US); Isaac Ostrovsky, Wellesley, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 561 days.

(21) Appl. No.: 10/667,550

(22) Filed: Sep. 22, 2003

(65) Prior Publication Data

US 2004/0059373 A1 Mar. 25, 2004

Related U.S. Application Data

(63) Continuation of application No. 09/510,816, filed on Feb. 23, 2000, now abandoned.

(51) Int. Cl.
*A61M 29/00* (2006.01)
(52) U.S. Cl. ............... 606/200; 604/96; 606/194
(58) Field of Classification Search ............... 606/200, 606/191; 604/96
See application file for complete search history.

(56) References Cited

U.S. PATENT DOCUMENTS

| | | | |
|---|---|---|---|
| 3,540,431 A | 11/1970 | Mobin-Uddin | |
| 3,952,747 A | 4/1976 | Kimmell, Jr. | |
| 4,425,908 A | 1/1984 | Simon | |
| 4,494,531 A | 1/1985 | Gianturco | |
| 4,619,246 A | 10/1986 | Molgaard-Nielsen et al. | |
| 4,643,184 A | 2/1987 | Mobin-Uddin | |
| 4,650,466 A | 3/1987 | Luther | |
| 4,817,600 A | 4/1989 | Herms et al. | |
| 4,832,055 A | 5/1989 | Palestrant | |
| 4,990,156 A | 2/1991 | Lefebvre | |
| 4,998,539 A | 3/1991 | Delsanti | |
| 5,035,706 A | 7/1991 | Gianturco et al. | |
| 5,217,484 A | 6/1993 | Marks | |
| 5,324,304 A | 6/1994 | Rasmussen | |
| 5,329,942 A | 7/1994 | Gunther et al. | |
| 5,370,657 A | 12/1994 | Irie | |
| 5,375,612 A | 12/1994 | Cottenceau et al. | |
| 5,383,887 A | 1/1995 | Nadal | |
| 5,601,595 A | 2/1997 | Smith | |
| 5,634,942 A | 6/1997 | Chevillon et al. | |
| 5,709,704 A | 1/1998 | Nott et al. | |
| 5,810,874 A | 9/1998 | Lefebvre | |
| 5,836,968 A | 11/1998 | Simon et al. | |
| 5,836,969 A | 11/1998 | Kim et al. | |
| 5,853,420 A | 12/1998 | Chevillon et al. | |
| 5,968,071 A | 10/1999 | Chevillon et al. | |
| 5,976,172 A | 11/1999 | Homsma et al. | |
| 6,013,093 A | 1/2000 | Nott et al. | |
| 6,241,746 B1 * | 6/2001 | Bosma et al. | 606/200 |
| 6,267,776 B1 | 7/2001 | O'Connell | |

FOREIGN PATENT DOCUMENTS

| | | |
|---|---|---|
| WO | WO 98/02112 | 1/1998 |
| WO | WO 00/66031 | 11/2000 |

* cited by examiner

*Primary Examiner*—Vy Q. Bui
(74) *Attorney, Agent, or Firm*—Crompton, Seager & Tufte LLC (57) ABSTRACT

A thrombus filter configured for placement within a blood vessel lumen defined by a blood vessel wall. Methods and devices for selectively reshaping the thrombus filter so that the lumen of the blood vessel is substantially unobstructed. The thrombus filter includes a generally cylindrical anchoring portion, and a generally conical filtering portion terminating at an apex.

21 Claims, 7 Drawing Sheets

INTRAVASCULAR FILTERING DEVICES AND METHODS

This is a continuation of application Ser. No. 09/510,816 filed on Feb. 23, 2000 now abandoned.

FIELD OF THE INVENTION

The present invention relates generally to filters for use inside blood vessels. More particularly, the present invention relates to thrombus filters which may be securely affixed at a selected location in the vascular system.

BACKGROUND OF THE INVENTION

There are a number of situations in the practice of medicine when it becomes desirable for a physician to place a filter in the vascular system of a patient. One of the most common applications for vascular filters is the treatment of Deep Venous Thrombosis (DVT). Deep Venous Thrombosis patients experience clotting of blood in the large veins of the lower portions of the body. These patients are constantly at risk of a clot breaking free and traveling via the inferior vena cava to the heart and lungs. This process is known as pulmonary embolization. Pulmonary embolization can frequently be fatal, for example when a large blood clot interferes with the life-sustaining pumping action of the heart. If a blood clot passes through the heart it will be pumped into the lungs and may cause a blockage in the pulmonary arteries. A blockage of this type in the lungs will interfere with the oxygenation of the blood causing shock or death.

Pulmonary embolization may be successfully prevented by the appropriate placement of a thrombus filter in the vascular system of a patient's body. Placement of the filter may be accomplished by performing a laparotomy with the patient under general anesthesia. However, intravenous insertion is often the preferred method of placing a thrombus filter in a patient's vascular system.

Intravenous insertion of a thrombus filter is less invasive and it requires only a local anesthetic. In this procedure, the thrombus filter is collapsed within a delivery catheter. The delivery catheter is introduced into the patients vascular system at a point which is convenient to the physician. The delivery catheter is then fed further into the vascular system until it reaches a desirable location for filter placement. The thrombus filter is then released into the blood vessel from the delivery catheter.

In the treatment of Deep Venous Thrombosis, a thrombus filter is placed in the inferior vena cava of a patient. The inferior vena cava is a large vessel which returns blood to the heart from the lower part of the body. The inferior vena cava may be accessed through the patient's femoral vein.

Thrombus filters may be placed in other locations when treating other conditions. For example, if blood clots are expected to approach the heart and lungs from the upper portion of the body, a thrombus filter may be positioned in the superior vena cava. The superior vena cava is a large vessel which returns blood to the heart from the upper part of the body. The superior vena cava may by accessed through the jugular vein, located in the patient's neck.

Once placed inside a blood vessel, a thrombus filter acts to catch and hold blood clots. The flow of blood around the captured clots allows the body's lysing process to dissolve the clots.

If a filter becomes loose while positioned in the lumen of a blood vessel, it may migrate to a position where it may be ineffective at capturing thrombi. Alternately, and more seriously, a loose thrombus filter may migrate to a dangerous or life threatening position. To reduce the likelihood of migration, a thrombus filter may include anchor members which penetrate the vessel walls.

The walls of the blood vessels are lined with a thin inner membrane which may be referred to as the intima or the endothelium. When this inner membrane is disrupted by a foreign object such as a thrombus filter the body responds in a process referred to as neointimal hyperplasia. As a result, the disrupted area of inner membrane is overgrown with a number of new cells. The anchor portions of the thrombus filter are encapsulated with new cell growth, referred to as endothelial growth.

Due to neointimal hyperplasia, thrombus filters placed in the blood vessel of patient become affixed in the blood vessel wails within two weeks after being implanted. Because the portions of the filter contacting the blood vessel wall become fixed in this way, many prior art filters cannot be removed percutaneously after being in place for more than two weeks.

SUMMARY OF THE INVENTION

The present invention relates to a thrombus filter configured for placement within a blood vessel lumen defined by a blood vessel wall. The present invention also relates to methods and devices for selectively reshaping the thrombus filter so that the lumen of the blood vessel is substantially unobstructed. One embodiment of a thrombus filter in accordance with the present invention includes a generally cylindrical anchoring portion and a generally conical filtering portion terminating at an apex. The filtering portion includes a plurality of elongate strands arranged in an overlapping pattern to create a plurality of cells. The cells of the filtering portion allow blood to flow through the filtering portion of the thrombus filter with little resistance. The cells also enable the filtering portion to trap, or capture blood clots traveling through the blood vessel lumen. The generally conical shape of the filtering portion urges captured blood clots toward the center of the blood flow. The flow of blood around the captured blood clots allows the body's natural lysing process to dissolve the clots.

The anchoring portion of the thrombus filter includes a plurality of elongated strands arranged to create anchoring cells. The anchoring portion of the thrombus filter is adapted to expand radially in size so that it conforms to the walls of the blood vessel. In a presently preferred embodiment, the anchoring portion exerts a radial force on the walls of the blood vessel. The radial force exerted by the anchoring portion of the thrombus filter reduces the likelihood that the thrombus filter will migrate within the lumen of the blood vessel.

In one embodiment of a thrombus filter in accordance with the present invention, a retaining means is disposed at the apex of the filter portion. The retaining means may include a coupling member fixed to its distal end. In this embodiment of the thrombus filter, the strands of the filter portion are biased to expand outward and conform to the shape of the lumen of the blood vessel. The retaining means is adapted to retain the distal ends of the filter strands and maintain the generally conical shape of the filtering portion.

A catheter in accordance with the present invention may be used to remove the retaining means from the thrombus filter. When the retaining means is removed, the filtering portion of the thrombus filter converts from a generally conical shape to a generally cylindrical shape. When the filtering portion assumes a cylindrical shape, the strands are disposed proximate the blood vessels walls leaving the lumen substantially unobstructed.

A catheter in accordance with one embodiment of the present invention includes a lumen, a distal end, and a proximal end. An elongate member is disposed in the lumen of the catheter. The elongate member includes a distal end, a proximal end and coupling member disposed proximate the distal end. The coupling member of the elongate member of the catheter is adapted to couple with the coupling member of the retaining means. The proximal end of the elongate member protrudes beyond the proximal end of the catheter. Both the catheter and the elongate member extend outside the body of the patient.

To remove the retaining means from the thrombus filter, the distal end of the catheter is first positioned over the apex of the thrombus filter. The coupling member of the elongate member is then coupled with the coupling member of the retaining means. The retaining means may then be urged off of the thrombus filter. In a presently preferred embodiment, a pulling force is used to urge the retaining means away from the thrombus filter. Also in a presently preferred embodiment, this pulling force is created by pulling on the proximal end of the elongate member.

An additional embodiment of a thrombus filter in accordance with the present invention has also been envisioned. This thrombus filter includes a generally cylindrical anchoring portion, and a generally conical filtering portion terminating at an apex. The filtering portion includes a plurality of filtering strands which converge at an apex to create a plurality of cells. In this embodiment of a thrombus filter, the filtering strands may be selectively deformed to convert the filtering portion from a generally conical shape to a generally cylindrical shape. When the filtering strands are selectively deformed to a cylindrical shape, they are disposed proximate the walls of the blood vessel leaving the vessel lumen substantially unobstructed.

A catheter in accordance with the present invention may be used to deform the strands of the filtering section of the thrombus filter. One embodiment of this catheter includes a distal end, and an expanding means disposed proximate the distal end. In a presently preferred embodiment, the catheter is a balloon catheter and the expanding means is a balloon. The catheter is urged forward within the vasculature of the patient until the expanding means is proximate the thrombosis filter. Specifically, the expansion means is positioned so that it is disposed within the filtering portion of the thrombus filter. The expansion means is then expanded. The expansion of the expansion means deforms the strands of the filter portion of the thrombus filter to a generally cylindrical shape. After the strands are deformed, they will be disposed proximate the walls of the blood vessel, leaving the blood vessel lumen substantially unobstructed.

DETAILED DESCRIPTION OF THE INVENTION

The following detailed description should be read with reference to the drawings, in which like elements in different drawings are numbered identically. The drawings which are not necessarily to scale, depict selected embodiments and are not intended to limit the scope of the invention.

Examples of constructions, materials, dimensions, and manufacturing processes are provided for selected elements. All other elements employ that which is known to those of skill in the field of the invention. Those skilled in the art will recognize that many of the examples provided have suitable alternatives which may be utilized.

Figure 1:
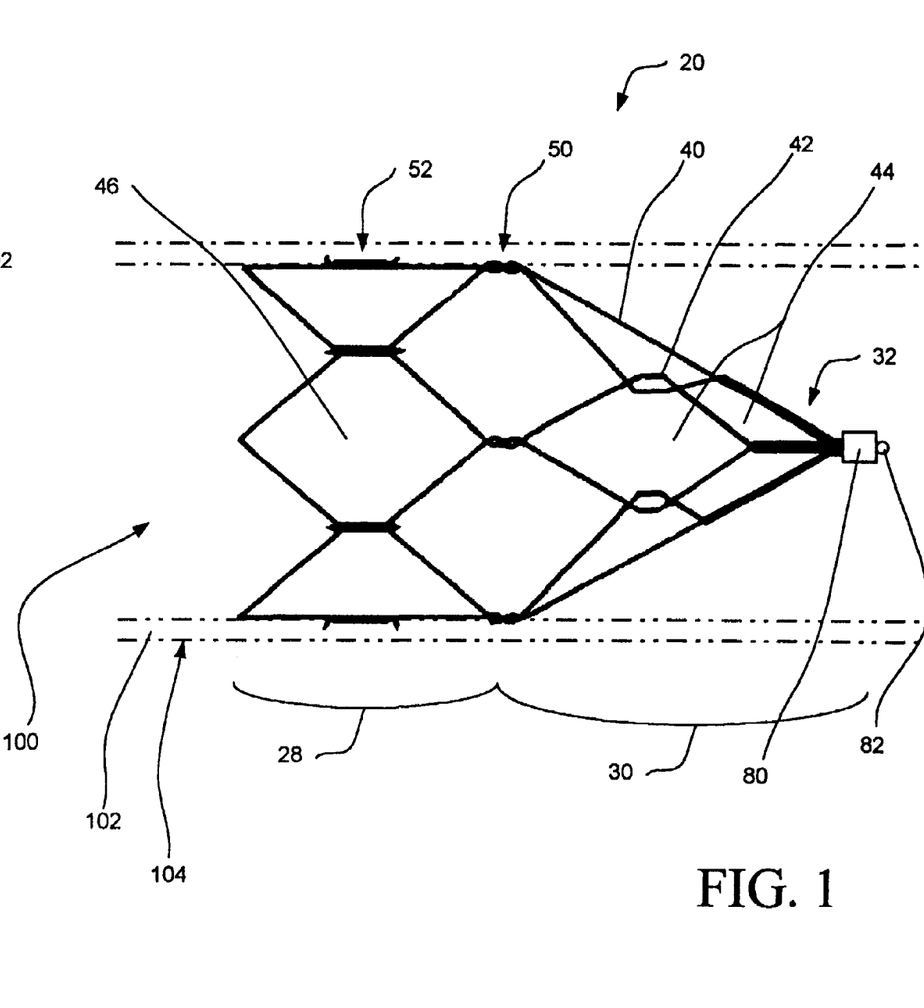
FIG. 1 is a plan view of a thrombus filter disposed in the lumen of a blood vessel.

Reference is now made to the drawings, in which like numbers refer to like elements throughout. FIG. 1 is a plan view of a thrombus filter 20 disposed in a lumen 100 defined by walls 102 of a blood vessel 104. Thrombus filter 20 includes a generally cylindrical anchoring portion 28, and a generally conical filtering portion 30 terminating at an apex 32.

Filtering portion 30 includes a plurality of elongated strands 40 including a plurality of bends 42. Strands 40 of filtering portion 30 are arranged in an overlapping pattern to create a plurality of cells 44. Cells 44 are best shown in FIG. 2.

Figure 2:
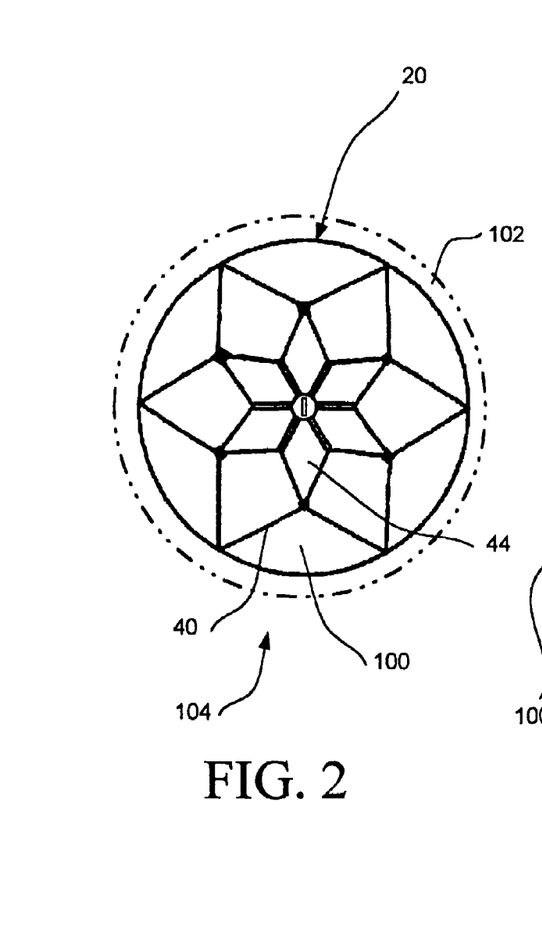
FIG. 2 is an axial plan view of the thrombus filter of FIG. 1.

FIG. 2 is an axial plan view of the thrombus filter 20 of FIG. 1. As described above, filtering portion 30 of thrombus filter 20 includes a plurality of cells 44. Cells 44 allow blood to flow through filtering portion 30 with little resistance. Cells 44 also enable filtering portion 30 to trap, or capture blood clots traveling though blood vessel 104. The generally conical shape of filtering portion 30 urges captured blood clots toward the center of the blood flow. The flow of blood around the captured blood clots allows the body's natural lysing process to dissolve the clots.

Referring again to FIG. 1, it may be appreciated that strands 40 extend beyond filtering portion 30 into anchoring portion 28. In the embodiment of FIG. 1, strands 40 are arranged to create anchoring cells 46. Anchoring portion 28 of thrombus filter 20 is adapted to expand in size so that it conforms to walls 102 of blood vessel 104. Anchoring portion 28 is adapted to exert a radial force on walls 102 of blood vessel 104. The radial force exerted by anchoring portion 28 on walls 102 of blood vessel 104 reduces the likelihood that thrombus filter 20 will migrate within lumen 100 of blood vessel 104.

Figure 3:
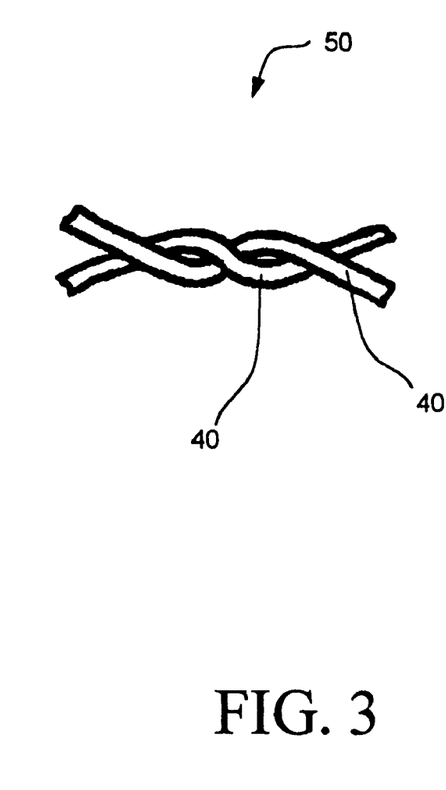
FIG. 3 is an enlarged plan view of a portion of the thrombus filter of FIG. 1.

As seen in FIG. 1, strands 40 are joined together at joined portions 50. FIG. 3 is an enlarged plan view of joined portion 50. In the embodiment of FIG. 3, joined portion 50 is created by twisting two strands 40 about eachother. Other methods may be used to form joined portions 50 without departing from the spirit or scope of the present invention. Examples, of methods which may be suitable in some applications include mechanical fastening, soldering, brazing, resistance welding, and tungsten inert gas welding.

Figure 4:
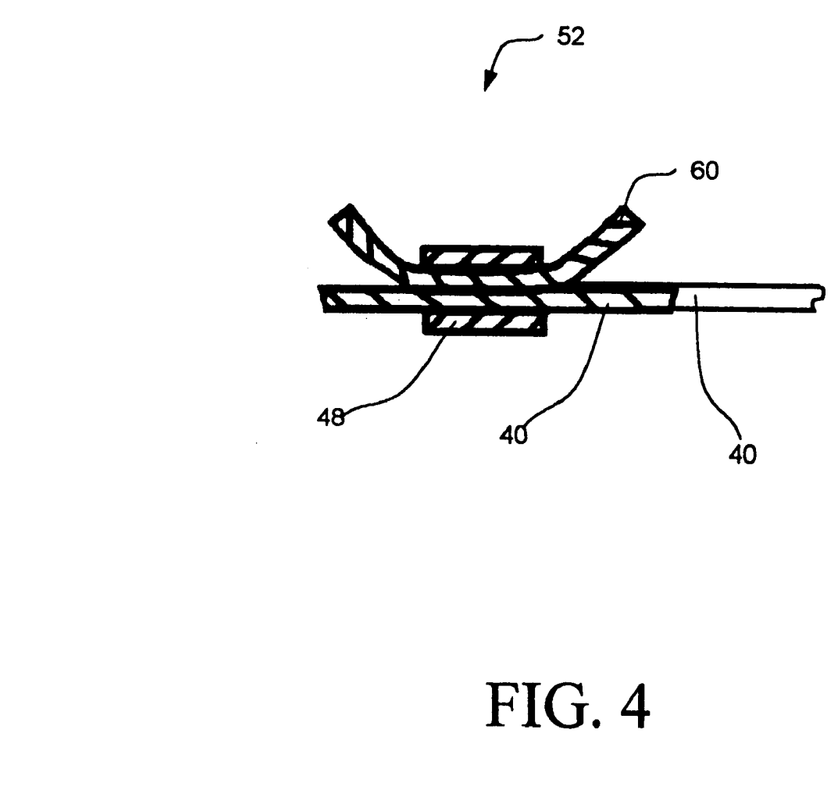
FIG. 4 is an enlarged plan view of a portion of the thrombus filter of FIG. 1.

Also in the embodiment of FIG. 1, cells 46 are joined together at joined portions 52. FIG. 4 is an enlarged plan view of joined portion 52. In the embodiment of FIG. 4, joined portion 52 is formed by passing two strands 40 and an anchor member 60 through a tubular member 48. In a presently preferred embodiment, tubular member 48 is comprised of metal tubing know in the art as hypotube. In this embodiment, anchor member 60 and one or more strands 40 pass through a lumen in a section of hypotubing. Also in a presently preferred embodiment, the hypotube section is fixed to the anchor member 60 and the one or more strands 40. A number of methods may be used to fix the hypotube section to the anchor member and the one or more strands 40. For example, a mechanical connection may be formed by crimping the hypotube. By way of a second example, the hypotube section may be soldered to the anchor member 60 and strands 40. Other processes which may be suitable in some applications include, brazing, resistance welding, and tungsten inert gas welding.

In a presently preferred embodiment, anchor members 60 include a sharp point capable of penetrating walls 102 of blood vessel 104. In this fashion, anchor members 60 reduce the likelihood that thrombus filter 20 will migrate upstream or downstream in lumen 100 of blood vessel 104.

Walls 102 of blood vessel 104 are lined with a thin inner membrane which may be referred to as the intima or the endothelium. When this inner membrane is disrupted by a foreign object such as a thrombus filter the body responds in a process referred to as neointimal hyperplasia. As a result, the disrupted area of inner membrane is overgrown with a number of new cells. The portions of a thrombus filter which are in contact with the intima will likely be encapsulated with new cell growth, referred to as endothelial growth.

In a presently preferred embodiment, strands 40 are generally circular in cross section. It should be understood that other cross-sectional shapes are possible without deviating from the spirit or scope of the invention. For example, the cross-sectional shape of stands 40 could be circular, rectangular, square, triangular, oval, etc.

In a presently preferred embodiment, strands 40 are comprised of a nickel titanium alloy. Suitable nickel titanium materials are commercially available from Memry Technologies (Brookfield, Conn.), TiNi Alloy Company (San Leandro, Calif.), and Shape Memory Applications (Sunnyvale, Calif.). Strands 40 may be comprised of other metallic or non-metallic materials without departing from the spirit or scope of the present invention. Examples of metallic materials which may be suitable for some applications include stainless steel. Suitable, non-metallic materials suitable may be selected from the following list, which is not exhaustive: poly(L-lactide) (PLLA), poly(D,L-lactide) (PLA), polyglycolide (PGA), poly(L-lactide-co-D,L-lactide) (PLLA/PLA), poly(L-lactide-co-glycolide) (PLLA/PGA), poly(D, L-lactide-coglycolide) (PLA/PGA), poly(glycolide-co-trimethylene carbonate) (PGA/PTMC), polyethylene oxide (PEO), polydioxanone (PDS), polycaprolactone (PCL), polyhydroxylbutyrate (PHBT), poly(phosphazene), polyD,L-lactide-co-caprolactone) (PLA/PCL), poly(glycolide-co-caprolactone) (PGA/PCL), polyanhydrides (PAN), poly(ortho esters), poly(phoshate ester), poly(amino acid), poly(hydroxy butyrate), polyacrylate, polyacrylamid, poly(hydroxyethyl methacrylate), polyurethane, polysiloxane and their copolymers.

In the embodiment of FIGS. 1-4, thrombus filter 20 includes a retaining means 80 disposed at apex 32 of filter portion 30. Retaining means 80 includes a coupling member 82 fixed to the distal end of retaining means 80. Strands 40 of filter portion 30 are biased to expand outward and conform to the shape of lumen 100 defined by walls 102 of blood vessel 104. Retaining means 80 is adapted to retain the distal ends of strands 40 and maintain the generally conical shape of filtering portion 30. In the embodiment of FIGS. 1-4, retaining means 80 is a collar which may be removed to selectively allow filter portion 30 to convert from a generally conical shape to a generally cylindrical shape. When filtering portion 30 assumes a cylindrical shape, strands 40 are disposed proximate walls 102 of blood vessel 104, leaving lumen 100 substantially unobstructed.

Other embodiments of retaining means 80 have been envisioned. For example, retaining means 80 may be comprised of a twisted pattern formed by twisting the ends of strands 40 together.

Figure 5:
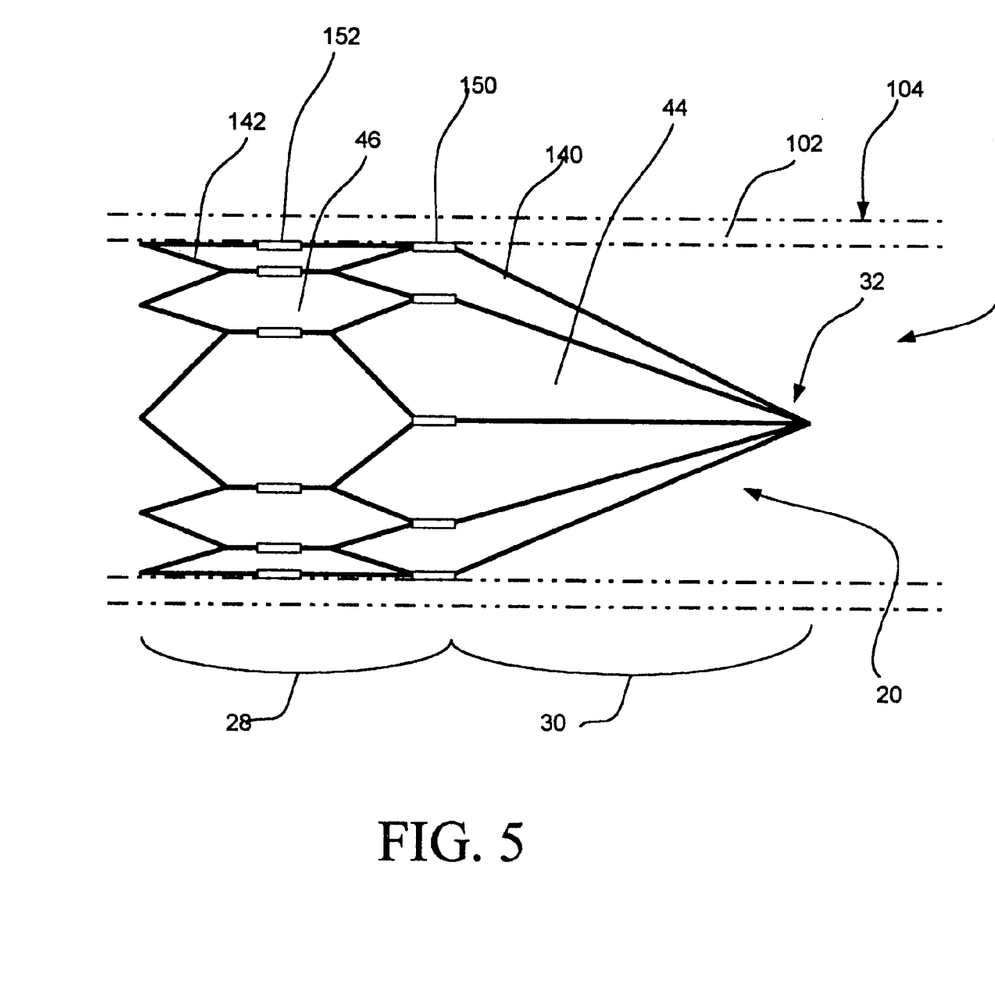
FIG. 5 is a plan view of an alternate embodiment of a thrombus filter in accordance with the present invention.

Other embodiments of thrombus filter 20 have also been envisioned. FIG. 5 is a plan view of an alternate embodiment of filter 20 in accordance with the present invention. Thrombus filter 20 of FIG. 5 includes a generally cylindrical anchoring portion 28, and a generally conical filtering portion 30 terminating at an apex 32. Filtering portion 30 includes a plurality of filtering strands 140 which converge at apex 32 to create a plurality of cells 44. Cells 44 are best shown in FIG. 6.

Figure 6:
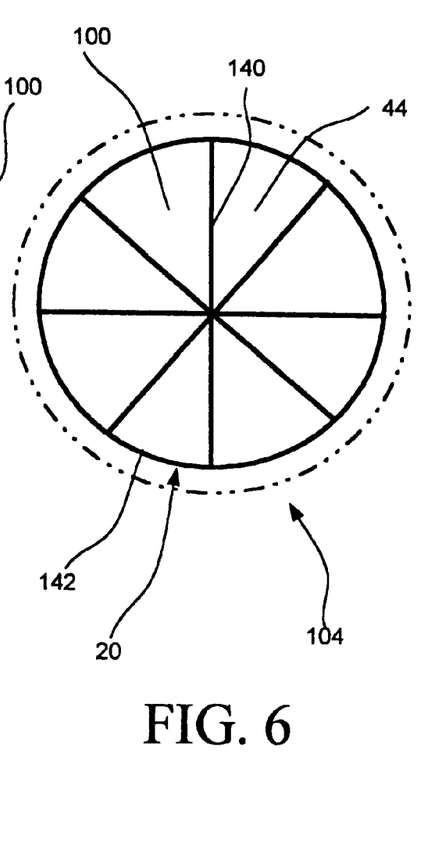
FIG. 6 is an axial plan view of the thrombus filter of FIG. 5.

FIG. 6 is an axial plan view of thrombus filter 20. As described above, filtering portion 30 of thrombus filter 20 includes a plurality of cells 44. Cells 44 allow blood to flow through filtering portion 30 with little resistance. Cells 44 also enable filtering portion 30 to trap, or capture blood clots traveling though the blood vessel. The generally conical shape of filtering portion 30 urges captured blood clots toward the center of the blood flow. The flow of blood around the captured blood clots allows the body's natural lysing process to dissolve the clots.

Referring again to FIG. 5, anchoring portion 28 of thrombus filter 20 includes a plurality of anchoring strands 142 which are arranged to create anchoring cells 46. Anchoring portion 28 of thrombus filter 20 is adapted to expand in size so that it conforms to walls 102 of blood vessel 104. Anchoring portion 28 is adapted to exert a radial force on walls 102 of blood vessel 104. The radial force exerted by anchoring portion 28 on walls 102 of blood vessel 104 reduces the likelihood that thrombus filter 20 will migrate within lumen 100 of blood vessel 104.

As seen in FIG. 5, anchoring strands 142 are joined to filter strands 140 at joining portions 150. Also in the embodiment of FIG. 5, each anchoring cell 46 is joined to one or more adjacent anchoring cells 46 by joining portions 152.

In a presently preferred embodiment, anchoring strands 142 are comprised of a nickel titanium alloy. Suitable nickel titanium materials are commercially available from Memry Technologies (Brookfield, Conn.), TiNi Alloy Company (San Leandro, Calif.), and Shape Memory Applications (Sunnyvale, Calif.). Those with skill in the art will appreciate that anchoring strands 142 may be comprised of other materials without departing from the spirit or scope of the present invention.

In the embodiment of FIG. 5, filtering strands 140 may be selectively deformed to convert filtering portion 30 from a generally conical shape to a generally cylindrical shape.

Figure 7:
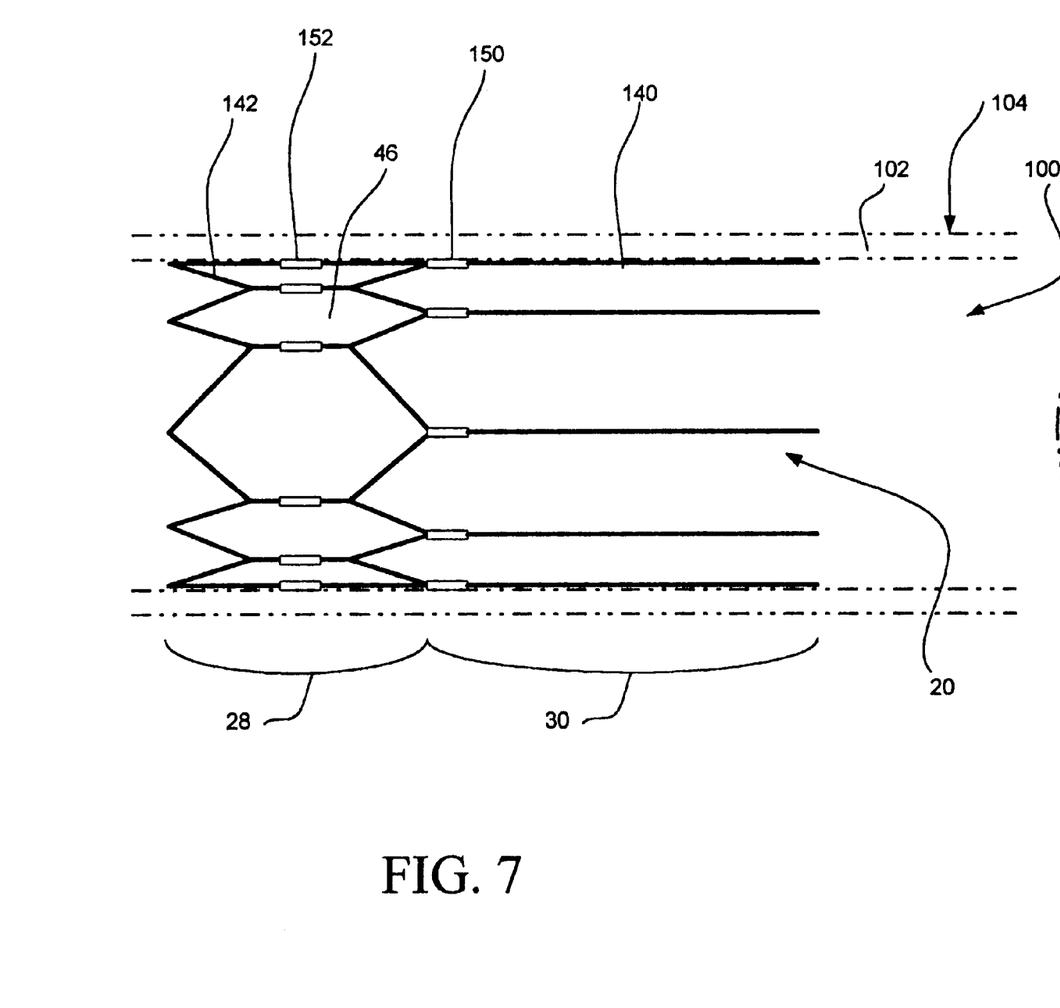
FIG. 7 is a plan view of the thrombus filter of FIG. 5 in a configuration which leaves the lumen of the blood vessel substantially unobstructed.
Figure 8:
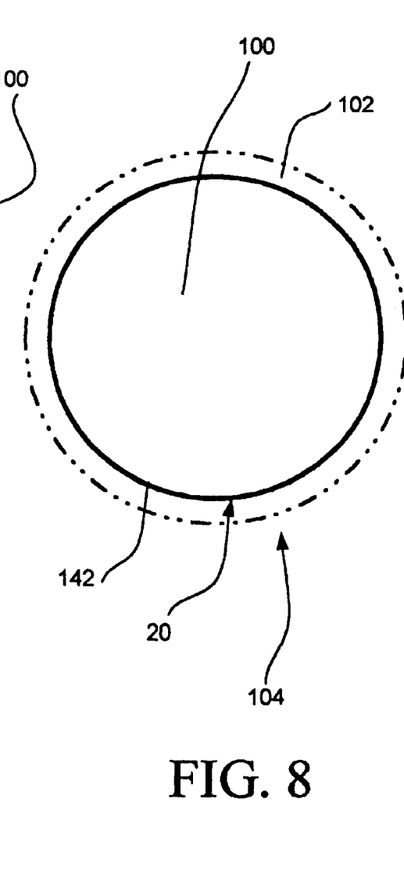
FIG. 8 is an axial plan view of a thrombus filter of FIG. 7.

FIG. 7 is a plan view of thrombus filter 20 with a generally cylindrical filtering portion 30. FIG. 8 is an axial plan view of view of thrombus filter 20 with filtering portion 30 selectively converted to a cylindrical shape. As shown in FIG. 8, strands 40 are disposed proximate walls 102 of blood vessel 104, leaving blood vessel lumen 100 substantially unobstructed.

A method of selectively converting thrombus filter 20 from the shape illustrated in FIGS. 5 and 6 to the shape illustrated in FIGS. 7 and 8 may now be described. A method of selectively converting a thrombus filter in accordance with the present invention would typically begin with the step of providing a catheter with an expanding means disposed at its distal end. In a presently preferred embodiment, the catheter is a balloon catheter and the expanding means is a balloon.

The catheter typically enters the patients vascular system at a point which is readily accessible to the physician. Once in the vascular system, the catheter is urged forward until the expanding means is proximate thrombus filter 20. Specifically, the expansion means is positioned so that it is disposed within filter portion 30. The expansion means is then expanded. The expansion of the expansion means deforms strands 140 of filter portion 30 to the generally cylindrical shape shown in FIGS. 7 and 8. As shown in FIGS. 7 and 8, strands 40 are disposed proximate walls 102 of blood vessel 104, leaving blood vessel lumen 100 substantially unobstructed.

Figure 9:
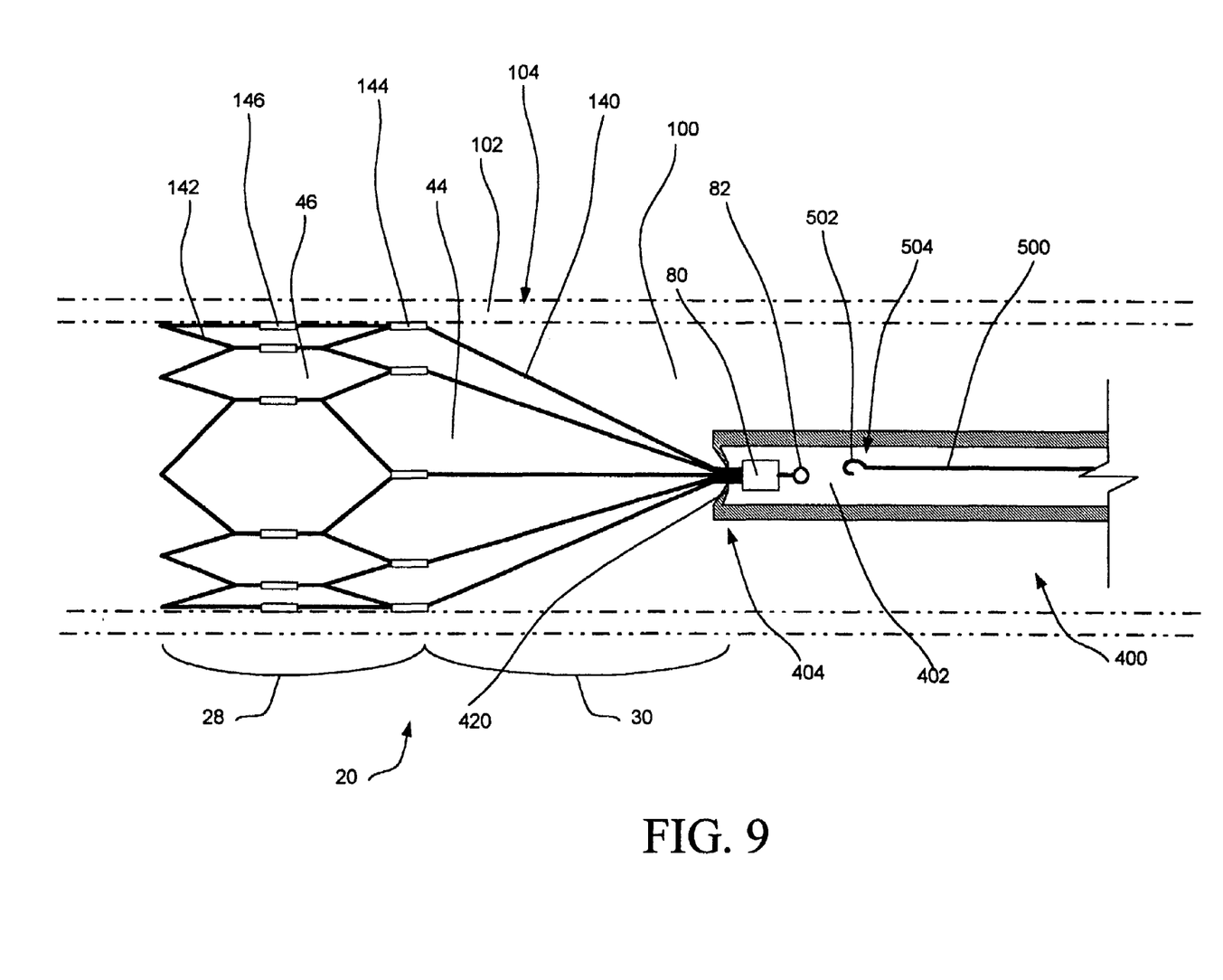
FIG. 9 is a plan view of an alternate embodiment of a thrombus filter in accordance with the present invention.

FIG. 9 is a plan view of an alternate embodiment of filter 20 in accordance with the present invention. Thrombus filter 20 of FIG. 9 includes a generally cylindrical anchoring portion 28, and a generally conical filtering portion 30 terminating at an apex 32.

Filtering portion 30 includes a plurality of filtering strands 140 which converge at apex 32 to create a plurality of cells 44. Anchoring portion 28 of thrombus filter 20 includes a plurality of anchoring strands 142 which are arranged to create anchoring cells 46. Anchoring portion 28 of thrombus filter 20 is adapted to expand in size so that it conforms to walls 102 of blood vessel 104. Anchoring portion 28 is adapted to exert a radial force on walls 102 of blood vessel 104. The radial force exerted by anchoring portion 28 on walls 102 of blood vessel 104 reduces the likelihood that thrombus filter 20 will migrate within lumen 100 of blood vessel 104.

As seen in FIG. 9, anchoring strands 142 are joined to filter strands 140 at joining portions 144. Also in the embodiment of FIG. 9, each anchoring cell 46 is joined to one or more adjacent anchoring cells by joining portions 146.

In a presently preferred embodiment, anchoring strands 142 and filter strands 140 are comprised of a nickel titanium alloy. Suitable nickel titanium materials are commercially available from Memry Technologies (Brookfield, Conn.), TiNi Alloy Company (San Leandro, Calif.), and Shape Memory Applications (Sunnyvale, Calif.). As in the previous embodiment, anchoring strands 140 may be comprised of other materials without departing from the spirit or scope of the present invention.

In the embodiment of FIG. 9, thrombus filter 20 includes a retaining means 80 disposed at apex 32 of filter portion 30. Filter strands 140 of filter portion 30 are biased to expand outward and conform to the shape of lumen 100 defined by walls 102 of blood vessel 104. Retaining means 80 is adapted to retain the distal ends of filter strands 140 and maintain the generally conical shape of filtering portion 30. In the embodiment of FIG. 9, retaining means 80 is a collar which may be removed to selectively allow filter portion 30 to convert from a generally conical shape to a generally cylindrical shape. When filtering portion 30 assumes a cylindrical shape, filter strands 140 are disposed proximate walls 102 of blood vessel 104, leaving blood vessel lumen 100 substantially unobstructed. Retaining means 80 includes a coupling member 82 fixed to the distal end of retaining means 80.

A catheter 400 which may be used to selectively reshape thrombus filter 20 is also illustrated in FIG. 9. Catheter 400 includes a lumen 402, a distal end 404, and a proximal end 406 (not shown). An elongate member 500 is disposed in lumen 402 of catheter 400. Elongate member 500 includes a distal end 504, a proximal end 506 (not shown), and a coupling member 502 disposed proximate distal end 504.

Coupling member 502 of elongate elongate member 500 is adapted to couple with coupling member 82 of retaining means 80. Proximal end 506 (not shown) of elongate member 500 protrudes beyond proximal end 406 of catheter 400. Both catheter 400 and elongate member 500 extend outside the body of the patient. Catheter 400 firther includes a retaining means 420. In the embodiment of FIG. 9, the distal end of catheter 400 is disposed over apex 32 of thrombus filter 20 such that retaining means 80 is disposed in lumen 402 of catheter 400.

A method of converting a thrombus filter in accordance the instant embodiment the present invention may be described with reference to FIG. 9. A catheter 400 with a lumen 402 and a distal end 404 is disposed in lumen 100 of blood vessel 104. Catheter 400 may enter the patients vascular system at a point which is readily accessible to the physician. Once in the vascular system, catheter 400 is urged forward until distal end 404 is proximate thrombus filter 20. For example, if thrombus filter 20 is located in the inferior vena cava of a patients vascular system, catheter 400 may enter the vascular system at the femoral vein. Alternately, if thrombus filter 20 is located in the superior vena cava of a patients vascular system, catheter 400 may enter the vascular system at the jugular vein. In either case, the filter conversion procedure is minimally invasive, and does not require general anesthesia.

Figure 10:
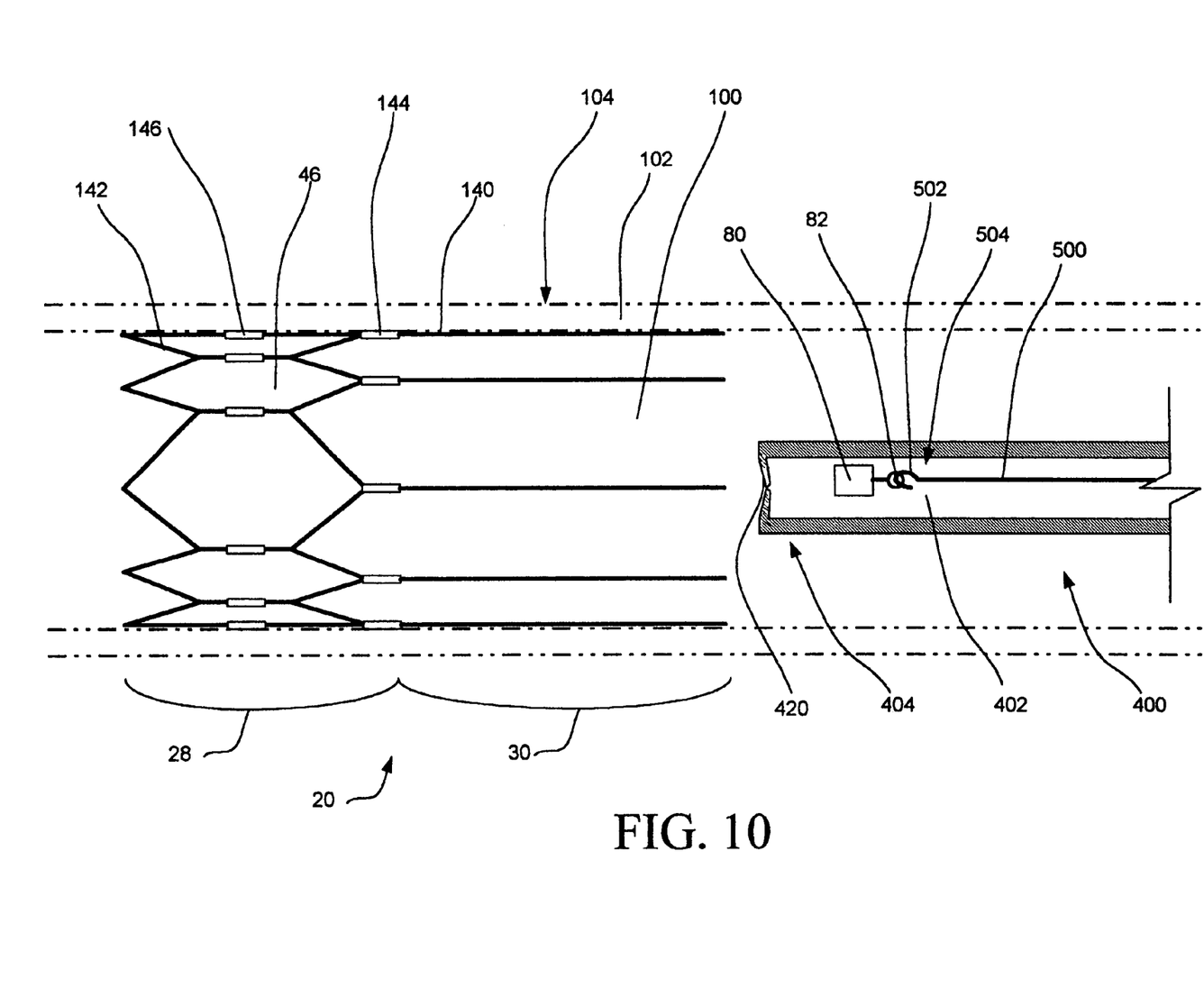
FIG. 10 is a plan view of the thrombus filter of FIG. 9 with the filter portion configured so that the lumen of the blood vessel is substantially unobstructed.

An elongated elongate member 500 including a distal end 504 and a proximal end 506 (not shown) is disposed in lumen 402 of catheter 400. In FIG. 10, distal end 404 of elongate member 500 has been mated to coupling member 82 of retaining means 80. Proximal end 506 of elongated elongate member 500 protrudes beyond proximal end 406 of catheter 400. Both catheter 400 and elongate member 500 extend outside the body of the patient.

When distal end 104 of catheter 400 reaches a position proximate thrombus filter 20, distal end 104 is urged further forward so that retaining means 80 of thrombus filter 20 is pushed into lumen 402 of catheter 400. Coupling member 502 of elongated elongate member 500 is then coupled to coupling member 82 of retaining means 80. With elongated elongate member 500 affixed to coupling member 82 of retaining means 80, retaining means 80 may be readily separated from thrombus filter 20 by applying a pulling force to proximal end 506 of elongate member 500. This pulling force is transferred via elongate member 500 to retaining means 80. The pulling force applied to elongate member 500 of thrombus filter 20 pulls retaining means 80 off of the distal ends of strands 40. Once retaining means 80 has been removed, strands 40 are free to spring outward allowing filtering portion 30 to assume a generally cylindrical shape. Once retaining means 80 is inside lumen 402; catheter 400 may be withdrawn from blood S vessel 104.

Retaining means 420 assures that retaining means 80 does not does not exit lumen 402 of catheter 400 and become loose in blood vessel 104.

Figure 11:
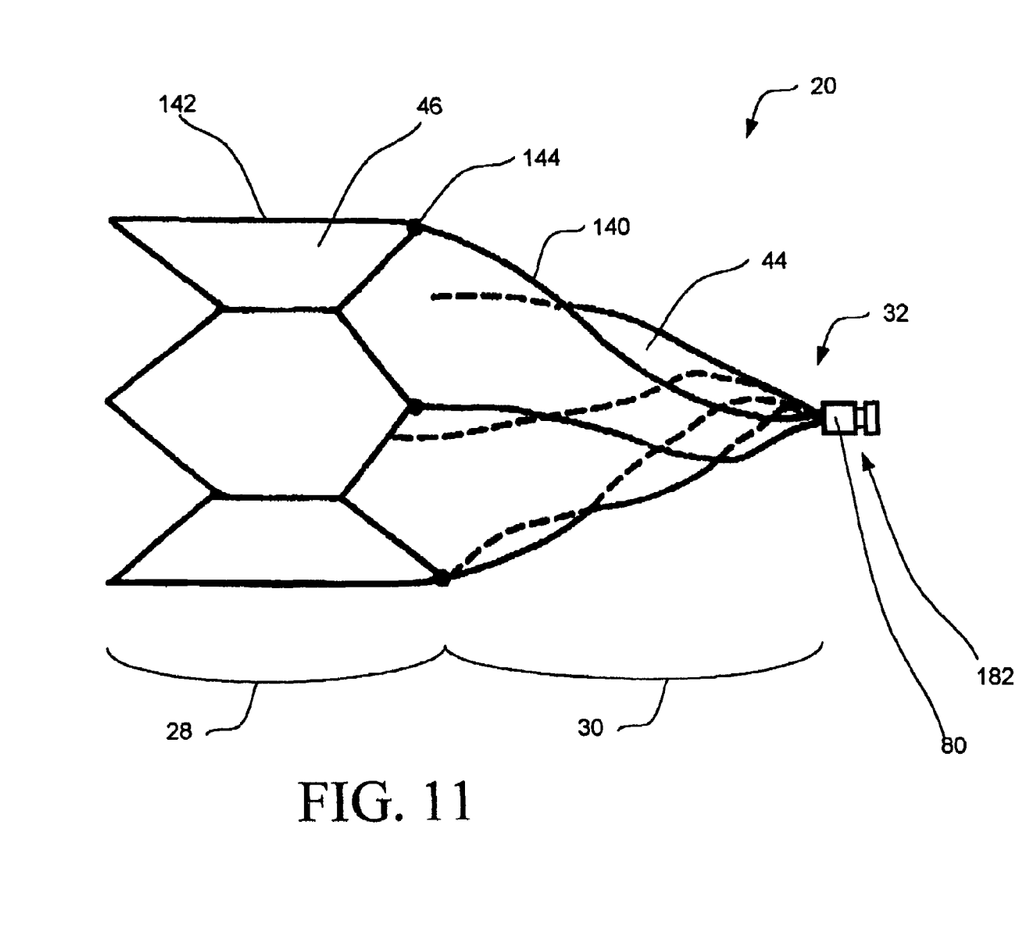
FIG. 11 is a plan view of an alternate embodiment of a thrombus filter in accordance with the present invention.

FIG. 11 is a plan view of an alternate embodiment of filter 20 in accordance with the present invention. Thrombus filter 20 of FIG. 11 includes a generally cylindrical anchoring portion 28, and a generally conical filtering portion 30 terminating at an apex 32.

Filtering portion 30 includes a plurality of filtering strands 140 which converge at apex 32 to create a plurality of cells 44. Anchoring portion 28 of thrombus filter 20 includes a plurality of anchoring strands 142 which are arranged to create anchoring cells 46. Anchoring portion 28 of thrombus filter 20 is adapted to expand in size so that it conforms to walls 102 of blood vessel 104. Anchoring portion 28 is adapted to exert a radial force on walls 102 of blood vessel 104. The radial force exerted by anchoring portion 28 on walls 102 of blood vessel 104 reduces the likelihood that thrombus filter 20 will migrate within lumen 100 of blood vessel 104.

As seen in FIG. 11, anchoring strands 142 are joined to filter strands 140 at joining portions 144. In the embodiment of FIG. 11, joining portions 144 are weld beads. A number of welding processes may be suitable for creating joining portions 144 of FIG. 11. For example, tungsten inert gas (TIG) welding, resistance welding, and LASER welding may all be suitable in some applications.

In the embodiment of FIG. 11, thrombus filter 20 includes a retaining means 80 disposed at apex 32 of filter portion 30. Filter strands 140 of filter portion 30 are biased to expand outward and conform to the shape of lumen 100 defined by walls 102 of blood vessel 104. Retaining means 80 is adapted to retain the distal ends of strands 40 and maintain the generally conical shape of filtering portion 30. In the embodiment of FIG. 11, retaining means 80 is a collar which may be removed to selectively allow filter portion 30 to convert from a generally conical shape to a generally cylindrical shape. When filtering portion 30 assumes a cylindrical shape, strands 40 are disposed proximate walls 102 of blood vessel 104, leaving blood vessel lumen 100 substantially unobstructed. Retaining means 80 includes a coupling element 182 proximate to the distal end of retaining means 80.

Figure 12:
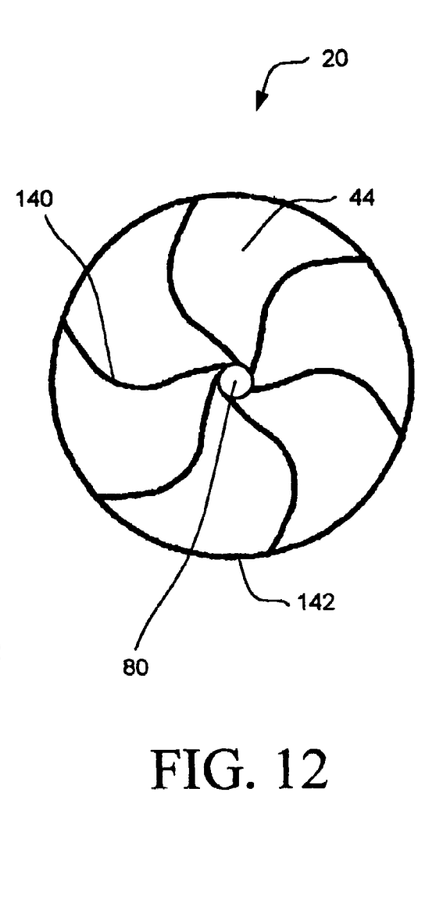
FIG. 12 is an axial plan view of the thrombus filter of FIG. 11.

FIG. 12 is an axial plan view of the thrombus filter 20 of FIG. 11. As best seen in FIG. 12, each filtering strand 140 is formed in generally helical, or spiraled shape. The diameter of the helix varies along the length of each filter strand 140 to form the generally conical shape of filter portion 30. As shown in FIG. 12, cells 44 defined by filter strands 140 are generally spiraled in nature.

Numerous advantages of the invention covered by this document have been set forth in the foregoing description. It will be understood, however, that this disclosure is, in many respects, only illustrative. Changes may be made in details, particularly in matters of shape, size, and arrangement of parts without exceeding the scope of the invention. The inventions's scope is, of course, defined in the language in which the appended claims are expressed.

What is claimed is:

1. A thrombus filter for placement within a blood vessel lumen defined by a blood vessel wall, comprising:
    a wall engaging portion comprised of a plurality of wall elements including a plurality of wall engaging strands;
    a filtering portion comprised of a plurality of filtering strands;
    a selectively releasable retainer disposed on the filtering strands;
    the filtering portion being fixed to the wall engaging portion;
    each wall engaging strand connected to each other wall engaging strand, either directly or solely through other wall elements; and
    a catheter disposed adjacent the thrombus filter, the catheter having a lumen and a capture member,
    wherein the catheter is configured to engage the selectively releasable retainer and the capture member is configured to retain the retainer within the lumen when the retainer has been released;
    wherein the wall elements include a plurality of tubular members having central lumens, the plurality of the tubular members having a portion of at least one wall engaging strand in the central lumen.

2. The filter of claim 1, wherein the plurality of wall elements are attached to at least one other wall element.

3. The filter of claim 1, wherein the plurality of wall elements are arranged to define a plurality of wall engaging cells.

4. The filter of claim 1, wherein the tubular members comprise an anchoring portion, each anchoring portion having a plurality of protrusions to anchor the tubular member to the blood vessel wall.

5. The filter of claim 1, wherein the wall elements comprise an anchoring member, each anchoring portion having a plurality of protrusions to anchor the anchoring member to the blood vessel wall.

6. The filter of claim 1, further comprising a shaft disposed within the catheter, the shaft being configured to engage the selectively releasable retainer.

7. The filter of claim 6, wherein the shaft is configured to remove the selectively releasable retainer from the filtering strands.

8. The filter of claim 7, wherein the catheter includes retaining means for maintaining the selectively releasable retainer within the catheter when the retainer is removed from the filtering strands.

9. The filter of claim 1, wherein a portion of two wall engaging strands are in the plurality of the tubular members.

10. A thrombus filter for placement within a blood vessel lumen defined by a blood vessel wall, comprising:
    a plurality of wail engaging strands connected together and defining a generally cylindrical wall engaging portion;
    a plurality of filtering strands each having a proximal end attached to the wall engaging portion and a distal end;
    wherein the filtering strands define a filtering portion that is configured to shift between a first generally conical shape and a second generally cylindrical shape, the filtering portion being biased to be in the second generally cylindrical shape; and
    a retainer releasably attached to the distal ends of the filtering strands that holds the filtering portion in the first generally conical shape; wherein the retainer includes a graspable collar;
    a catheter having a lumen and a capture member, the catheter being configured to engage the retainer and the capture member being configured to retain the retainer within the lumen when the retainer has been released.

11. The filter of claim 10, wherein the retainer includes a graspable loop.

12. The filter of elaim 10, further comprising a catheter configured to engage the retainer.

13. The filter of claim 12, further comprising a shaft disposed within the catheter, the shaft being configured to engage the retainer.

14. The filter of claim 13, wherein the shaft is configured to remove the retainer from the distal ends of the filtering strands.

15. The filter of claim 14, wherein the catheter includes retaining means for maintaining the retainer within the catheter when the retainer is removed from the distal ends of the filtering strands.

16. A thrombus filter, comprising:
a cylindrical wall engaging region defined by a plurality of connected wall engaging strands;
a filtering region defined by a plurality of filtering strands each having a proximal end attached to the wall engaging portion and a distal end;
wherein the filtering region is configured to shift between a first generally conical shape and a second generally cylindrical shape, the first generally conical shape is defined by the distal ends of the filtering strands converging and being closely associated with one another, the second generally cylindrical shape is defined by the distal ends of the filtering strands diverging and separating from one another;
wherein the filtering region is biased to be in the second generally cylindrical shape;
a retainer releasably attached to the distal ends of the filtering strands that holds the filtering region in the first generally conical shape, wherein the retainer includes a graspable collar; and
a catheter configured to engage the retainer, the catheter including retaining means for maintaining the retainer within the catheter when the retainer is removed from the distal ends of the filtering strands.

17. The filter of claim 16, wherein the retainer includes a graspable loop.

18. The filter of claim 16, further comprising a shaft disposed within the catheter, the shaft being configured to engage the retainer.

19. The filter of claim 18, wherein the shaft is configured to remove the retainer from the distal ends of the filtering strands.

20. A thrombus filter, comprising:
a cylindrical wall engaging region, wherein the wall engaging region includes a plurality of tubular members having central lumens;
a filtering region having a proximal end attached to the wall engaging portion and a distal end;
wherein the filtering region is configured to shift between a first generally conical shape and a second generally cylindrical shape, the first generally conical shape is defined when the distal end of the filtering region is closed, the second generally cylindrical shape is defined when the distal end of the filtering region is open;
wherein the filtering region is biased to be in the second generally cylindrical shape; and
means for controlling the shape of the filtering region releasably attached to the distal end of the filtering region;
a catheter configured to engage a retainer, the catheter including a retaining means for maintaining the means for controlling the shape of the filtering region within the catheter when the means for controlling the shape of the filtering region is released from the distal end of the filtering region.

21. A thrombus filter, comprising:
a cylindrical wall engaging portion defined by a plurality of connected wall engaging filaments;
a filtering portion defined by a plurality of filtering filaments each having a proximal end attached to the wall engaging portion and a distal end;
wherein the filtering portion is configured to shift between a first generally conical shape and a second generally cylindrical shape;
wherein the filtering portion is biased to be in the second generally cylindrical shape;
a retainer releasably attached to the distal ends of the filtering filaments that holds the filtering portion in the first generally conical shape; and
a catheter configured to engage the retainer, the catheter including retaining means for maintaining the retainer within the catheter when the retainer is removed from the distal ends of the filtering filaments;
wherein the wall engaging portion includes a plurality of tubular members having central lumens, the plurality of the tubular members having a portion of at least one wall engaging filament in the central lumen.

* * * * *